United States Patent [19]

Weber et al.

[11] 4,317,925

[45] Mar. 2, 1982

[54] PROCESS FOR THE PRODUCTION OF DI-N-PROPYLACETIC ACID

[75] Inventors: Jürgen Weber, Oberhausen; Wolfgang Bernhagen, Mulheim/Ruhr; Helmut Springer, Oberhausen, all of Fed. Rep. of Germany

[73] Assignee: Ruhrchemie Aktiengesellschaft, Oberhausen, Fed. Rep. of Germany

[21] Appl. No.: 60,559

[22] Filed: Jul. 25, 1979

[30] Foreign Application Priority Data

Oct. 13, 1978 [DE] Fed. Rep. of Germany ....... 2844636

[51] Int. Cl.$^3$ .................. C07C 51/235; C07C 53/128
[52] U.S. Cl. .................................... 562/531; 562/606; 568/450; 568/462; 568/596; 568/691
[58] Field of Search ............................... 562/531, 606; 260/601 R; 568/691, 450, 462, 596

[56] References Cited

U.S. PATENT DOCUMENTS 4,127,604 11/1978 Chignac .............................. 562/606

FOREIGN PATENT DOCUMENTS 7605350 11/1976 U.S.S.R. .............................. 562/606

Primary Examiner—Vivian Garner
Attorney, Agent, or Firm—Sprung, Felfe, Horn, Lynch & Kramer

[57] ABSTRACT

A process for the preparation of di-n-propylacetic acid which comprises the steps of A. converting n-valeraldehyde-diallyl acetal into allyl-1-pentenyl ether by cleaving one mol of allyl alcohol per one mol of n-valeraldehyde-diallyl acetal;
B. rearranging the allyl-1-pentenyl ether thermally into 2-propyl-pent-4-en-1-al,
C. partially hydrogenating the 2-propyl-pent-en-1-al catalytically to form 2-propyl valeraldehyde, and
D. oxidizing the 2-propyl valeraldehyde to form dipropyl-acetic acid.

3 Claims, No Drawings

PROCESS FOR THE PRODUCTION OF DI-N-PROPYLACETIC ACID

BACKGROUND OF THE INVENTION

1. Field of the Invention

The invention relates to a new process for the production of di-n-propylacetic acid from n-valeraldehyde.

2. Discussion of the Prior Art

Derivatives of di-n-propylacetic acid have gained great importance as psychopharmacologic drugs and antiepileptics. Several syntheses for the production of the acid have already been described.

In a known process, the starting material is malonic acid diethyl ester which is reacted initially with sodium methylate and then with allyl chloride to from di-allyl-diethyl malonate. Saponification with sodium hydroxide gives the sodium salt of diallyl malonic acid which is thermally decarboxylated to form diallyl acetic acid and subsequently hydrogenated partially to form di-n-propylacetic acid. The process requires the use of expensive starting materials which are difficult to handle technically such as sodium methylate and allyl chloride.

Another mode of operation for the preparation of di-isopropylacetic acid is described by Sarel in J. Am. Chem. Soc. 78, 5416–5420 (1956). In this process, cyanoacetic acid ester is alkylated in the presence of sodium isopropylate by means of isopropylate by means of isopropyl iodide. This results in the formation of diisopropyl-cyanoacetic acid ester which is decarboxylated to form diisopropylacetonitrile. In further steps, the diisopropylacetonitrile is converted into diisopropylacetic acid via diisopropylacetic acid amide. The application of this reaction route to the synthesis of di-n-propylacetic acid results, however, into total yields of only 10 to 40% and, therefore, is commercially unattractive.

East German Pat. No. 129,776 describes a process for the production of di-n-propylacetic acid which starts from an ester of cyanoacetic acid. Reaction with n-propyl bromide or iodide in the presence of sodium-n-propylate, saponification of the di-n-propyl-cyanoacetic acid ester by means of caustic and acidification result in 2,2-di-n-propylcyanoacetic acid which is decarboxylated to form di-n-propylacetonitrile. The substituted acetonitrile is subsequently saponified with aqueous sulfuric acid via the acetamide to form di-n-propylacetic acid. This process also uses expensive starting materials and requires the use of reaction steps which cannot be carried out continuously. Moreover, since the hydrolysis of acetamide to form the acid is carried out in the presence of sodium nitrite, problems in connection with environmental pollution are encountered.

It is an object of this invention, therefore, to provide a process for the preparation of di-n-propylacetic acid which starts from inexpensive starting materials which are available in commercial amounts, comprises reaction steps which are readily carried out commercially and provides the desired product in satisfactory yields.

SUMMARY OF THE INVENTION

The foregoing requirements are surprisingly met by a process for the production of di-n-propylacetic acid, which process comprises the steps of:

A. converting n-valeraldehyde-diallylacetal into a allyl-1-pentenyl ether by cleaving one mol of allyl alcohol per one mol of n-valeraldehyde-diallyl acetal, B. rearranging the allyl-1-pentenyl ether thermally into 2-propyl-pent-4-en-1-al, C. partially hydrogenating the 2-propyl-pent-4-en-1-al catalytically to form 2-propylvaleraldehyde, and D. oxidizing the 2-propylvaleraldehyde to form di-n-propyl acetic acid.

The process according to the invention commences with a conversion of n-valeraldehyde-diallylacetal into allyl-1-pentenyl ether. The n-valeraldehyde-diallylacetal can be prepared from valeraldehyde which is reacted with allyl alcohol in a molar ratio of 1:2, if desired also with excess alcohol, in the presence of an acidic catalyst such as toluene sulfonic acid or a cation exchanger used in concentrations of 0.01 to 2.0% by weight, based valeraldehyde, to form n-valeraldehyde-diallyl acetal. The diacetal is converted into allyl-1-pentenyl ether while cleaving one mol of allyl alcohol per mol of n-valeraldehyde-diallyl acetal. The cleavage of the diacetal is effected thermally by heating to 120° to 200° C. The presence of a solvent is necessary when forming the acetal because it serves as entrainer for the removal of the reaction liquor formed during the acetalization. Examples of suitable solvents include n-hexane, n-hexene, cyclohexane. The presence of a solvent is not necessary but also not detrimental for the acetal cleavage. Cleavage can be performed with or without a solvent. Useful solvents include those used for formation of the diacetal.

The thermal decomposition of the diallyl acetal is followed by a thermally induced reaction of the type of a Claisen rearrangement which leads to formation of 2-propyl-pent-4-en-1-al. The rearrangement takes place at temperatures of 250° to 350° C. The thermal rearrangement is effected for at least 1 second and up to 6 seconds.

According to an expedient varient of the mode of operation described above, the 2-propyl-pent-4-en-1-al may also be prepared from n-valeraldehyde in a single-step reaction; n-valeraldehyde and allyl alcohol are, deviating from the multi-step mode of operation, refluxed at 100° to 160° C. in a molar ratio of 2:1 to 0.9:1, especially about 1:1 in the presence of a catalytic amount, e.g., 0.01 to 2.0 weight percent of an acid, e.g., p-toluene sulfonic acid, especially an acid of pKa of 0.50 to 4.36, e.g., benzosulfonic acid, ortho-phosphoric-acid, sulfanilic-acid or p-toluic-acid in a high-boiling solvent, e.g., isododecane of diphenyl. In this reaction, there is initially formed the whole acetal (diacetal) of n-valeraldehyde which is cleaved under the reaction conditions, i.e., a temperature to form the unsaturated ether and directly rearranged to form 2-propyl-pent-4-en-1-al despite the relatively low temperature.

The 2-propyl-pent-4-en-1-al having been prepared as described above is then hydrogenated to form the saturated aldehyde. The reaction with hydrogen is carried out in the presence of a hydrogenation catalyst, especially a noble metal hydrogenation catalyst, at temperatures of 60° to 120° C. and under a hydrogen pressure of 60 to 100 bars. Palladium/charcoal supported catalysts having a palladium content of 0.2 to 10.0% by weight, based on total catalyst, have been found to be particularly advantageous for this hydrogenation. They are used in a concentration of 1.0 to 5.0% by weight, based on the weight of the reaction mixture, the amount of catalyst depending upon the palladium content thereof. The reaction is carried out in the liquid phase. It is effective to use a hydrogen/2-propyl-pent-4-en-1-al mol ratio of 1:1 to 20:1. It proceeds very selectively and permits hydrogenation of the double bond without a conversion of the aldehyde into the corresponding alcohol taking place.

The 2-propyl pentenal obtained by hydrogenation of 2-propyl-pent-4-en-1-al is oxidized with oxygen at 20° to 60° C. to form di-n-propyl acetic acid. The oxidation is expediently carried out in a tubular reactor provided with distributor trays. Oxygen may be used in pure form or in the form of gas mixtures, e.g., air. The presence of a catalyst has been found to be desirable to suppress the formation of by-products and reduce the reaction time. Examples of suitable catalysts include the sodium and potassium salts of di-n-propyl acetic acid or lead or barium chromate. Catalyst are used in a concentration of 0.1 to 2.0% by weight, based on the reaction mixture. The conversion of the aldehyde into the corresponding acid takes place almost quantitatively.

To prepare di-n-propyl acetic acid in pure form, the oxidation products are processed by distillation. Distillation is desirably carried out under subatmospheric pressure, e.g., a pressure of 1 to 400 Torr.

The new process for the production of di-n-propyl acetic acid has substantial advantages as compared with known processes. The starting materials, i.e., n-valeraldehyde and allyl alcohol, are commercially produced base chemicals which are available at low cost. The operations to be carried out during the course of the synthesis can be performed without any difficulty on a commercial scale, and essential partial steps of the overall process, e.g., the partial hydrogenation and the oxidation, may be carried out continuously. Finally, time-consuming and expensive operations for the recovery of chemicals which, in other known processes, must be used as auxiliary materials for the synthesis of intermediate compounds are unnecessary.

The new mode of operation is illustrated in greater detail in the example which follows:

EXAMPLE

1840 Grams (10 moles) of n-valeraldehyde diallyl acetal which is producible in analogous manner by known methods (see, for example, Houben-Weyl, Vol. VII/1, p. 419) in good yields are distilled in a 1 meter column having 24 theoretical plates in such a manner that a bottoms temperature of about 180° C. and an overhead temperature of about 140° C. are established under an operating pressure of 100 Torr and at a reflux ratio of 0.5:1. Under the reaction conditions, the whole acetal is cleaved quantitatively to form chiefly allyl-1-pentenyl ether which already partially undergoes rearrangement to form 2-propyl-pent-4-en-1-al. The yield (determined as the sum of allyl-1-pentyl ether, isomeric ethers and 2-propyl-pent-4-en-1-al) is 96%.

The mixture is subjected to thermal rearrangement in an electrically heated tube which is provided with an intense condenser. The tube is filled with Raschig rings (5×4 mm.). The volume of the tube is 380 ml. The liquid is supplied to the tube by means of a metering pump at a rate of 570 ml/hr. corresponding to a space velocity of 1.5 at a temperature of 300° C. Crude 2-propyl-pent-4-en-1-al in an amount of 1764 g. is obtained from 1786 g. of starting mixture. By fractional distillation, 1150 g. of 99.5% 2-propyl-pent-4-en-1-al are obtained therefrom (yield, 95%).

The distilled unsaturated aldehyde is partially hydrogenated in an autoclave. The reaction is carried out at a temperature of T=80° C. and a hydrogen pressure of $P_{H2}=80$ bars in the presence of a palladium catalyst. The hydrogenation is terminated after about 4 hours. The hydrogenation product is separated from the catalyst. There are obtained 1109 g. of pure 2-propyl-pentanal (yield, 95%) which are oxidized in a glass tube which is suitable for oxidation by means of oxygen gas in the presence of about 1% of the sodium salt of di-propyl acetic acid at a temperature of T=30° C. to form di-n-propyl acetic acid.

After processing by distillation, 1122 g. of 99.1% di-n-propyl-acetic acid are obtained (yield, 90%). The 1122 g. of di-n-propyl-acetic acid obtained from 1840 g. of complete acetal correspond to a total yield of 78%. The following characteristics were found for the distilled acid: b.p.$_{10\ Torr}$=118° C.; $n_D^{20}$=1.4249; $D_d^{20}$=0.905.

What is claimed is:

1. A process for the preparation of di-n-propylacetic acid which comprises the steps of:
    A. converting n-valeraldehyde-diallyl acetal into allyl-1-pentenyl ether by cleaving one mol of allyl alcohol per one mol of n-valeraldehyde-diallyl acetal at a temperature of 120° to 200° C.;
    B. rearranging the allyl-1-pentenyl ether so formed by heating the same at a temperature of 250° to 350° C. to convert the same into 2-propyl-pent-4-en-1-al;
    C. partially hydrogenating the 2-propyl-pent-4-en-1-al catalytically to form 2-propyl-valeraldehyde and
    D. oxidizing the 2-propyl-valeraldehyde at 20° to 60° C. by contacting the same with an oxygen-containing gas.

2. A process according to claim 1 wherein the n-valeraldehyde diallyl acetal converted according to step A is prepared by contacting valeraldehyde with allyl alcohol in the presence of an acidic catalyst and a solvent.

3. A process according to claim 1 wherein said 2-propyl-pent-4-en-1-al is hydrogenated by contacting the same with hydrogen in the presence of a noble metal hydrogenation catalyst at a temperature of 60° to 120° C. under a hydrogen pressure of 60 to 100 bars to form 2-propyl-valeraldehyde.

* * * * *